(12) United States Patent
McConnell et al.

(10) Patent No.: US 10,815,192 B2
(45) Date of Patent: Oct. 27, 2020

(54) U-47700 IMMUNOASSAY

(71) Applicant: Randox Laboratories Ltd., Crumlin, County Antrim (GB)

(72) Inventors: Ivan McConnell, Crumlin (GB); Peter Fitzgerald, Crumlin (GB); Elouard Benchikh, Crumlin (GB); Philip Lowry, Crumlin (GB)

(73) Assignee: Randox Laboratories Ltd., Crumlin (IE)

( * ) Notice: Subject to any disclaimer, the term of this patent is extended or adjusted under 35 U.S.C. 154(b) by 226 days.

(21) Appl. No.: 15/903,361

(22) Filed: Feb. 23, 2018

(65) Prior Publication Data
US 2018/0237380 A1  Aug. 23, 2018

(30) Foreign Application Priority Data
Feb. 23, 2017 (GB) .................................. 1702907.5

(51) Int. Cl.
| | | |
|---|---|---|
| *C07C 233/79* | (2006.01) | |
| *C07K 16/18* | (2006.01) | |
| *G01N 33/94* | (2006.01) | |
| *G01N 33/53* | (2006.01) | |
| *C07K 16/44* | (2006.01) | |
| *C07K 16/16* | (2006.01) | |

(52) U.S. Cl.
CPC ............ *C07C 233/79* (2013.01); *C07K 16/16* (2013.01); *C07K 16/18* (2013.01); *C07K 16/44* (2013.01); *G01N 33/5308* (2013.01); *G01N 33/9486* (2013.01); *C07K 2317/33* (2013.01)

(58) Field of Classification Search
CPC ...... C07C 233/79; C07K 16/16; C07K 16/18; C07K 16/44; C07K 2317/33; G01N 33/5308; G01N 33/9486
See application file for complete search history.

(56) References Cited

U.S. PATENT DOCUMENTS

2003/0224447 A1* 12/2003 McConnell ............ C07K 16/44
435/7.1

OTHER PUBLICATIONS

Goldsby et al., "Immunology," W.H. Freeman & Co., 2003, 5th Edition, p. 69.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Peterson et al., "Using hapten design to discover therapeutic monoclonal antibodies for treating methamphetamine abuse," J. Pharmacol. Exp. Ther., Jul. 2007; vol. 322, No. 1, pp. 30-39. Epub Apr. 23, 2007.*
Englebienne, "Immune and Receptor Assays in Theory and Practice," CRC Press, 2000, p. 308.*
Alpha Diagnostic International, Product Data Sheet, Cat# 700-101, "Keyhole limpet hemocyanin (KLH, hemocyanin) coated ELISA plates," retrieved from https://www.4adi.com/product/pdf/700-101.pdf on Feb. 20, 2020, which PDF was created/modified Apr. 10, 2013.*
Elliott et al., "The first reported fatality associated with the synthetic opioid 3,4-dichloro-N-[2-(dimethylamino) cyclohexyl]-N-methylbenzamide (U-47700) and implications for forensic analysis", Drug Testing and Analysis, 2016, 8(8):875-9.
Jones et al., "A case of U-47700 overdose with laboratory confirmation and metabolite identification", Clinical Toxicology, 2017, 55(1): 55-59.
World Health Organization (2016)—U-47700 Critical Review Report, Expert Committee on Drug Dependence, 38th Meeting, Geneva Nov. 14-18, 2016.

\* cited by examiner

*Primary Examiner* — Galina M. Yakovleva
(74) *Attorney, Agent, or Firm* — Gavrilovich, Dodd & Lindsey LLP

(57) ABSTRACT

Antibodies, immunoassay methods and kits for the detection and determination of 3,4,-dichloro-N-[2-(dimethylamino) cyclohexyl]-N-methylbenzamide and 3,4,-dichloro-N-[2-(methylamino)cyclohexyl]-N-methylbenzamide, as well as the precursory immunogens, are described.

9 Claims, 5 Drawing Sheets

U-47700 desmethyl U-47700 desmethylhydroxy U-47700 didesmethyl U-47700 didesmethylhydroxy U-47700

(a) 40% aqueous methylamine, 30 °C to room temperature.
(b) (i) Chlorosulfonic acid, Et$_2$O, 0 °C; (ii) 6N NaOH, 100 °C, 2.5 hours.
(c) (i) 40% aqueous methylamine, NH4Cl, 100 °C overnight; (ii) 6N NaOH, 100 °C, 2.5 hours.
(d) 3,4-Dichlorobenzoyl chloride, TEA, THF, 0 °C, 2 hours.
(e) (i) 1-Chloroethylchloroformate, THF, 0 °C than reflux overnight; (ii) MeOH, 60 °C, 6 hours.
(f) *tert*-Butyl acrylate, DIPEA, DMAP, ACN, reflux overnight.
(g) TFA/CH$_2$Cl$_2$, room temperature, overnight.

*FIG. 3*

(i) Bromoacetic acid HCTL, K$_2$CO$_3$, DMF

*FIG. 4*

|  | U-47700 | | AH-7921 | | Desmethyl U-47700 | |
|---|---|---|---|---|---|---|
| ng/ml | Ave OD | B/Bo | Ave OD | B/Bo | Ave OD | B/Bo |
| 0.000 | 1.617 | 100 | 1.592 | 100 | 1.620 | 100 |
| 0.3125 | 1.105 | 68 | 1.568 | 98 | 1.370 | 85 |
| 0.625 | 0.791 | 49 | 1.445 | 91 | 1.136 | 70 |
| 1.125 | 0.692 | 43 | 1.536 | 96 | 1.035 | 64 |
| 2.500 | 0.509 | 31 | 1.475 | 93 | 0.893 | 55 |
| 5.000 | 0.356 | 22 | 1.462 | 92 | 0.708 | 44 |
| 10.000 | 0.229 | 14 | 1.380 | 87 | 0.539 | 33 |
| 20.000 | 0.150 | 9 | 1.310 | 82 | 0.385 | 24 |

| IC50 | 0.722 | >>20.000 | 3.610 |
|---|---|---|---|
| %CR | 100 | <<3.610 | 20.000 |

|  | MT-45 | | Nor AH-7921 | | U-50488 | |
|---|---|---|---|---|---|---|
| ng/ml | Ave OD | B/Bo | Ave OD | B/Bo | Ave OD | B/Bo |
| 0.000 | 1.589 | 100 | 1.478 | 100 | 1.464 | 100 |
| 0.3125 | 1.592 | 100 | 1.528 | 103 | 1.463 | 100 |
| 0.625 | 1.469 | 92 | 1.381 | 93 | 1.311 | 90 |
| 1.125 | 1.579 | 99 | 1.480 | 100 | 1.377 | 94 |
| 2.500 | 1.600 | 101 | 1.463 | 99 | 1.446 | 99 |
| 5.000 | 1.622 | 102 | 1.425 | 96 | 1.358 | 93 |
| 10.000 | 1.660 | 104 | 1.418 | 96 | 1.385 | 95 |
| 20.000 | 1.637 | 103 | 1.351 | 91 | 1.288 | 88 |

| IC50 | >>20.000 | >>20.000 | >>20.000 |
|---|---|---|---|
| %CR | <<3.610 | <<3.610 | <<3.610 |

*FIG. 5*

U-47700 IMMUNOASSAY

CROSS REFERENCE TO RELATED APPLICATIONS

This application claims priority under 35 U.S.C. § 119 to Great Britain Application No. 1702907.5, filed Feb. 23, 2017, the disclosure of which is incorporated herein by reference for all purposes.

BACKGROUND 3,4-Dichloro-N-[2-(dimethylamino)cyclohexyl]-N-methylbenzamide, commonly known as U-47700, is a psychoactive synthetic drug of the opioid class. Pharmacologically similar to morphine, and a structural isomer of the synthetic opioid AH-7921 (EP3056518), it has addictive potential and has been implicated in a number of deaths (World Health Organisation 2016). Its pharmacological profile suggests a strong affinity for the mu-opioid receptor and that the main metabolic pathway involves demethylation at the amino of the cyclohexyl ring producing 3,4-dichloro-N-[(2-(methylamino)cyclohexyl]-N-methylbenzamide (synonyms nor-U-47700 or desmethyl U-47700). As with most of the recent abused synthetic psychoactive substances, it originates from the pharmaceutical industry (Elliot 2016). To date detection of the parent drug and metabolites has been effected using laboratory-based mass-spectrometry (e.g. Elliot 2016, Jones 2017), the equipment for which is expensive and requires highly-trained operators.

REFERENCES

World Health Organization (2016)—U-47700 Critical Review Report, Expert Committee on Drug Dependence 38th Meeting, Geneva 14-18 Nov. 2016.

Elliot S. P. et al (2016). *Drug Testing and Analysis*, 8(8): 875-9.

Jones M. J. et al (2017). *Clinical Toxicology*, 55(1): 55-59.

SUMMARY

Described herein is an immunoassay for the selective detection and determination of 3,4-dichloro-N-[2-(dimethylamino)cyclohexyl]-N-methylbenzamide and 3,4-dichloro-N-[2-(methylamino)cyclohexyl]-N-methylbenzamide. Also described are novel immunogens and their method of synthesis, novel and highly sensitive antibodies derived from the immunogens and kits incorporating the antibodies. The antibodies are highly specific to U-47700 and desmethyl U-47700 and have no measurable binding to closely related synthetic opiates such as AH-7921.

DETAILED DESCRIPTION

In a first aspect the invention is an immunogen of Structure I

Structure I wherein the accm is an antigenicity conferring carrier material (accm); suitable accms include polypeptides, proteins and protein fragments (or other polyamino acid containing compounds). Examples of antigenicity conferring carrier materials are keyhole limpet haemocyanin (KLH), bovine thyroglobulin (BTG), bovine serum albumin (BSA), egg ovalbumin, bovine gamma globulin or cationised BSA. Alternatively, synthetic polyamino acids having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. A hapten is a pre-immunogenic molecule e.g. Structure I without the accm. The accm of the invention is preferably chosen from KLH, BTG, BSA or egg ovalbumin. To form the immunogen the accm is attached to a molecule which incorporates the epitopic target; this is achieved using a crosslinker (a functionalised spacing and linking group). The crosslinker is standard in the field of antibody production (e.g. Wild, The Immunoassay Handbook 4th edition 2013, Chapter 3.4 Conjugation Methods) and like the accm can be varied in the immunogen without undermining the binding characteristics of the subsequently produced antibody. The crosslinker of Structure I is usually not more than 10 discrete chemical units in length, a discrete chemical unit being an atom or recognisable moiety such as a benzene ring, a heterocyclic ring, a sulphonyl group, an ester group, an amide group etc. The crosslinker of Structure I is preferably a substituted or unsubstituted, saturated or unsaturated alkylene moiety preferably of chain length $C_{1-10}$, more preferably $C_{1-6}$ i.e. for $C_{1-6}$ this represents methylene, ethylene, propylene, butylene, pentylene or hexylene; the substituents of the substituted alkylene can be further alkylene chains. Alkylene refers to a divalent alkyl moiety. Exemplary crosslinkers are —$CH_2$—C(O)—N—$CH_2$—($CH_2$—$CH_2$—SH)—C(O)— and —C(O)$_m$—($CH_2$)$_n$—Y— in which m=0 or 1, n=1, 2, 3, 4, 5 or 6 and Y is —(CO)—, —NH— or S e.g. —$CH_2$—$CH_2$—C(O)—. The latter, —$CH_2$—$CH_2$—C(O)—, is an example of a crosslinker with an alkylene of $C_2$ chain length and a carbonyl substituent i.e. three discrete chemical units in total and —$CH_2$—C(O)—N—$CH_2$—($CH_2$—$CH_2$—SH)—C(O)— is an example of a crosslinker with an alkylene of $C_1$ chain length and an amide group, a methylene group, a thioethylene substituent (three discrete units) and a carbonyl group i.e. seven discrete chemical units in total. 3,4-dichloro-N-[2-(dimethylamino)cyclohexyl]-N-methylbenzamide and its demethylated metabolite contain two chiral centers resulting in four possible stereoisomers (for the parent cis-(1R,2R)—U-47700, cis-(1S,2S)—U-47700, trans-(1R,2S)—U-47700 and trans-(1S,2R)—U-47700, for the demethylated metabolite cis-(1R,2R)-nor-U-47700, cis-(1S,2S)-nor-U-47700, trans-(1R,2S)-nor-U-47700 and trans-(1S,2R)-nor-U-47700), their corresponding stereospecific haptens and immunogens can be obtained using standard methods and incorporated individually or in combination in all aspects of the described invention.

A further aspect of the invention describes antibodies raised from any of the immunogens described in the previous paragraph. Preferably the antibodies have a cross-reactivity of 100% to 3,4-dichloro-N-[2-(dimethylamino) cyclohexyl]-N-methylbenzamide and a cross-reactivity of >10% to 3,4-dichloro-N-[2-(methylamino)cyclohexyl]-N-methylbenzamide; in a further embodiment the antibodies have a cross-reactivity of 100% to 3,4-dichloro-N-[2-(dimethylamino)cyclohexyl]-N-methylbenzamide and a cross-reactivity of >10% and <100% to 3,4-dichloro-N-[2-(methylamino)cyclohexyl]-N-methylbenzamide. In addition to or independently of these cross-reactivity profiles, it is preferable that the antibodies have an $IC_{50}$ of <5.00 ng/ml to 3,4-dichloro-N-[2-(dimethylamino)cyclohexyl]-N-methyl benzamide as this ensures that low concentrations of the opiate can be detected. For a highly sensitive assay an $IC_{50}$ of <1.00 ng/ml to 3,4-dichloro-N-[2-(dimethylamino) cyclohexyl]-N-methyl benzamide is preferred. The sensitivities of the antibodies can be measured by any suitable metric used in the art such as the limit of detection, limit of quantitation as well as the $IC_{50}$.

The invention also comprises an immunoassay method of detecting or determining 3,4-dichloro-N-[2-(dimethylamino)cyclohexyl]-N-methylbenzamide and 3,4-dichloro-N-[2-(methylamino)cyclohexyl]-N-methylbenzamide in a solution or an in vitro sample taken from an individual using one or more detecting agents and an antibody of the invention; and deducing the presence of, or amount of, 3,4-dichloro-N-[2-(dimethylamino) cyclohexyl]-N-methylbenzamide and 3,4-dichloro-N-[2-(methylamino)cyclohexyl]-N-methylbenzamide. In a preferred embodiment the antibody used in the method is derived from an immunogen of the invention. By 'detecting' is meant qualitatively analysing for the presence or absence of a substance; by 'determining' is meant quantitatively analysing for the amount of substance present. It is common practice that in the immunoassay method the presence or amount of target analyte(s) (in the current instance 3,4-dichloro-N-[2-(dimethylamino)cyclohexyl]-N-methylbenzamide and 3,4-dichloro-N-[2-(methylamino)cyclohexyl]-N-methylbenzamide) is gauged by reference to one or more calibrator values usually in the form of a cut-off value or calibration curve; the Immunoassay Development section herein describes the use of a calibrator to construct a calibration curve or 'standard curve' which allows the sensitivity (in this case the $IC_{50}$) and cross-reactivity of antibodies to the target analytes to be derived. However, it is possible that detection of the signal originating from the detecting agent does not make use of a calibrator—this possibility applies to the method of the invention. The in vitro sample is any suitable biological sample such as, but not limited to, blood, serum, plasma, urine or saliva. The in vitro sample is preferably a serum, plasma or urine sample. The solution can be a liquid suspected of containing one or more of these drugs. Alternatively, as these drugs can be in tablet or plant form e.g. sold as a herbal product, analysis of drugs suspected of containing these psychoactive ingredients may require pre-treatment to achieve a formulation suitable for analysis, such as dissolution in a suitable liquid. The immunoassay method is most suited to the competitive assay format in which a target analyte which binds to the antibody i.e. the molecule to be detected or determined, competes with a detecting agent (also called a 'tracer' or 'conjugate') which also binds to the antibody, for binding sites on the antibody; the more analyte present the less detecting agent that binds to the antibody and the lower the measured signal. The detecting agent can be a substance such as an enzyme, a substance having fluorescent properties or a radioactive label; it is usual for an immunoassay that the detecting agent is a structure similar to the target analyte in which an enzyme or a substance having fluorescent properties has been conjugated, or in which a radiolabel has been incorporated. Conjugation is by way of standard methods familiar to the skilled person. Typically enzymes promote light emission from substrates added to the assay medium. The 'detecting and determining' criteria for the immunoassay method includes, as is well-known in the art, detection of a signal, exceeding a pre-defined cut-off/concentration value or measuring the calibrator equivalent value as derived from a calibrator curve (also referred to as a standard curve). In relation to the antibodies described herein, in the context of the current invention, 'from which they are raised' is synonymous with 'to which they are derived'. Due to intermolecular attractive forces such as hydrogen bonding and van der Waal's forces there is often a degree of binding or affinity between two molecules whatever their respective structures; the skilled person recognizes that no cross-reactivity or minimal cross-reactivity implies that in the context of a working immunoassay any binding or interaction between an antibody and non-target analytes is at such a low level that it does not compromise the integrity of the immunoassay i.e. false positives are avoided. The antibodies of the invention, separate of or as part of the immunoassay method described, do not display cross-reactivity to any compounds which could undermine the immunoassay method.

The invention further comprises a substrate with which the antibodies of the invention engage. The antibodies can engage with the substrate by, for example, passive adsorption or can be chemically bonded to the substrate attached by way of, for example, covalent bonds. Such covalent bonding generally requires the initial introduction of a chemically active compound covalently attached to the substrate surface prior to antibody addition. The antibody itself may also require the addition of a chemical activating group to achieve substrate bonding. These requirements are well known in the art. The substrate can be any medium capable of adsorbing or bonding to an antibody, for example a bead or nanoparticle (optionally chemically-activated), but is preferably of a planar conformation (optionally chemically-activated) such as a microtitre plate or biochip. A biochip is a thin, wafer-like substrate with a planar surface which can be made of any suitable material such as glass or plastic but is preferably made of ceramic. The biochip is able to be chemically-activated prior to antibody bonding or is amenable to the passive adsorption of antibodies. The skilled person in biochip development for immunoassay application will recognize that a planar surface at high resolution e.g. if using a scanning electron microscope, is not perfectly 'flat' but will possess an uneven surface, the important aspect being that the 'approximately' planar surface is suitable for application. A microlayer coating of material can optionally be added to the planar surface of the substrate prior to antibody placement. Either the upper surface or both surfaces of the substrate can be coated. An advantage of the U-4700 targeted antibodies of the invention is that they can be used to detect other opiates or other drugs of abuse simultaneously in a multi-analyte or multiplex immunoassay test format, by-passing the need for multiple individual drug tests and thus reducing testing time and sample volume requirements; the planar biochip substrate is particularly amenable to this multi-analyte testing format. Other single compound-specific or family-specific antibodies of other drugs of abuse which can be incorporated onto the substrate, include antibodies that bind to other opiates (synthetic or natural), to synthetic cannabinoids, LSD, salvinorin, ketamine, mephedrone, methamphetamine, amphetamine and MDMA.

The invention further comprises a kit incorporating an antibody of the invention. The antibody is preferably attached to a microtitre plate or biochip; the kit can also incorporate a tracer and any further reagents necessary to enable a detectable or measurable signal to be produced.

General Methods, Examples and Results

Haptens, Crosslinkers, Immunogens and Detecting Agents

In immunology, haptens (can be referred to as 'small molecules') are defined as chemicals which by themselves cannot elicit immune responses; they require chemical coupling to larger immunogenic molecules (the accm), to be capable of inducing an immune response. As stated, acorns are well known in the art and can be any material that makes all or part of the hapten immunogenic. The process of immunogen formation generally involves coupling of the hapten to a crosslinking agent, the latter subsequently coupled to an accm. Alternatively, the crosslinker can be attached to the accm, followed by conjugation of hapten. It is also possible to couple a hapten directly to the accm. The concept of accm-(crosslinker)$_n$-hapten conjugation to form an immunogen, where n=0 or 1, is well-established; the conjugation and exact point of attachment of a hapten to a crosslinker must be adapted to the particular hapten and is guided by synthetic organic chemistry and immunology principles. Numerous crosslinkers and accms are commercially available and have been described in the literature (Thermo Scientific Crosslinking Technical Handbook, 1606073 April 2009; Bioconjugate Techniques G. Hermanson, ed, Academic Press, 1996, 785 pp—lists common carrier proteins). An example of a crosslinking group is 4-N-maleimidomethylcyclohexyl-1-carboxylic acid NHS ester solution (available from Sigma-Aldrich catalogue number 5525). An alternative crosslinker which can used to couple to haptens possessing a carboxylic acid is EDC and sulfo-NHS both of which are known in the art and are commercially available. In order to confirm that adequate conjugation of hapten to carrier material has been achieved, prior to immunization, each immunogen is evaluated using matrix-assisted UV laser desorption/ionization time-of-flight mass spectroscopy (MALDI-TOF MS). The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof.

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analyzed was diluted in 0.1% aqueous trifluoroacetic acid (TFA) to create 1 mg/ml sample solutions. Aliquots (1 µl) were analyzed using a matrix of sinapinic acid and bovine serum albumin (Fluke) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilized on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunizing an animal, preferably a mammalian animal, by repeated administration of an immunogen. The serum from the immunized animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal using standard techniques. The signal emitted in the immunoassay is proportionate to the amount of detecting agent bound to the antibodies which in turn is inversely proportionate to the analyte concentration. The signal can be detected or quantified by comparison with a calibrator.

EXAMPLES

Figure 1:
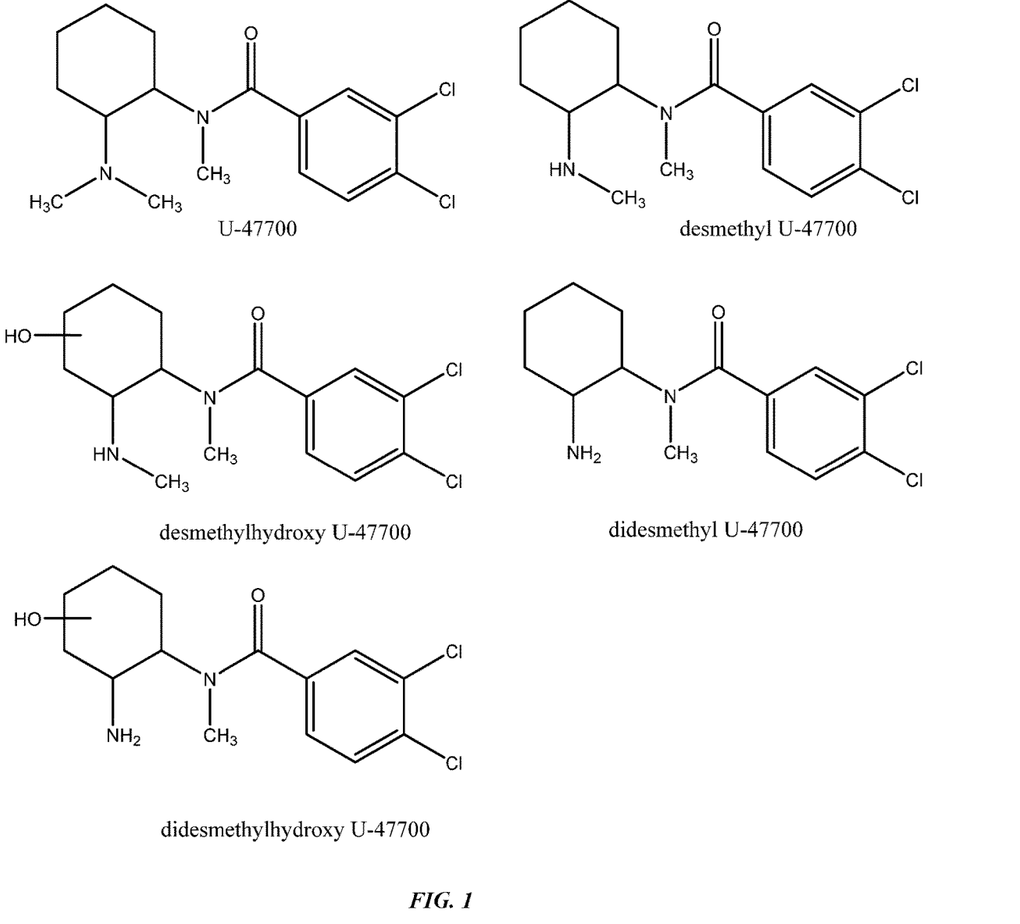
FIG. 1 shows 3,4-Dichlorobenzamido opiates and metabolites.
Figure 2:
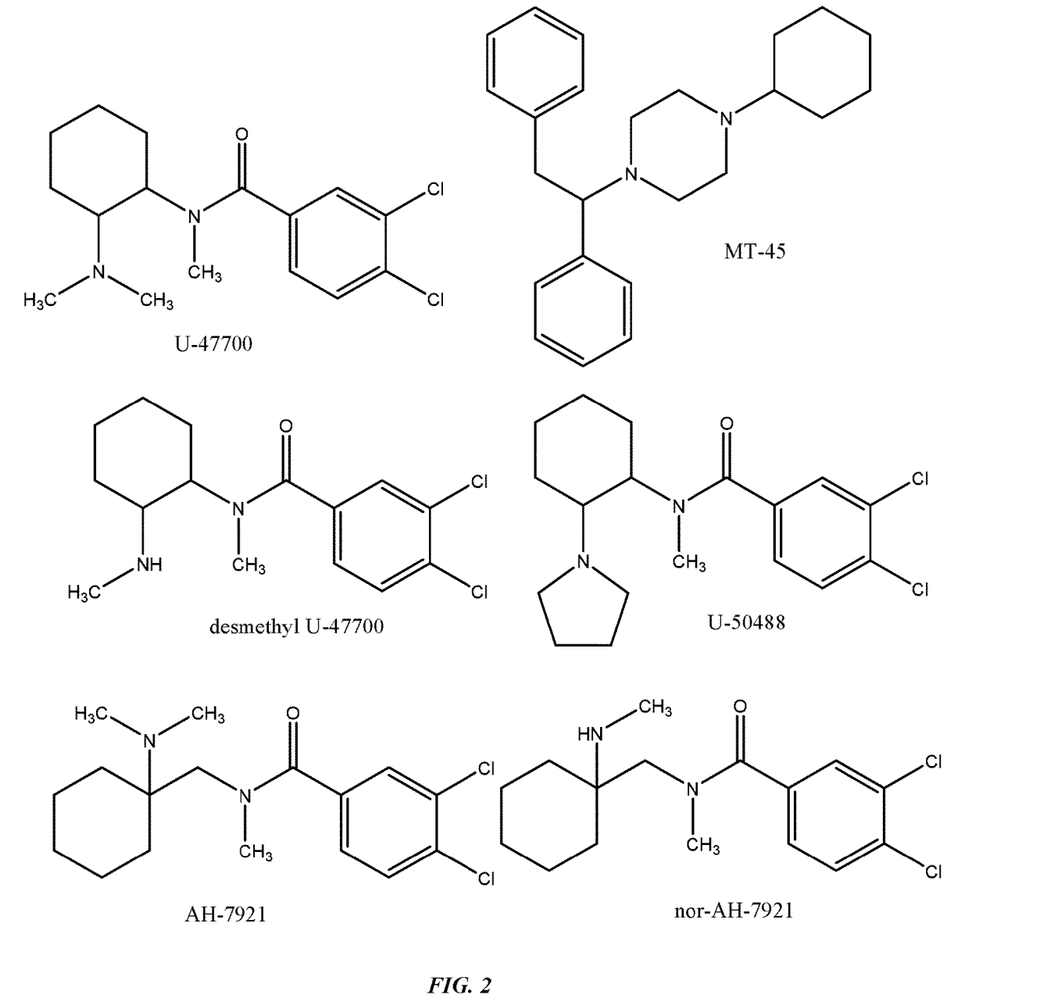
FIG. 2 shows Metabolites of U-47700.
Figure 3:
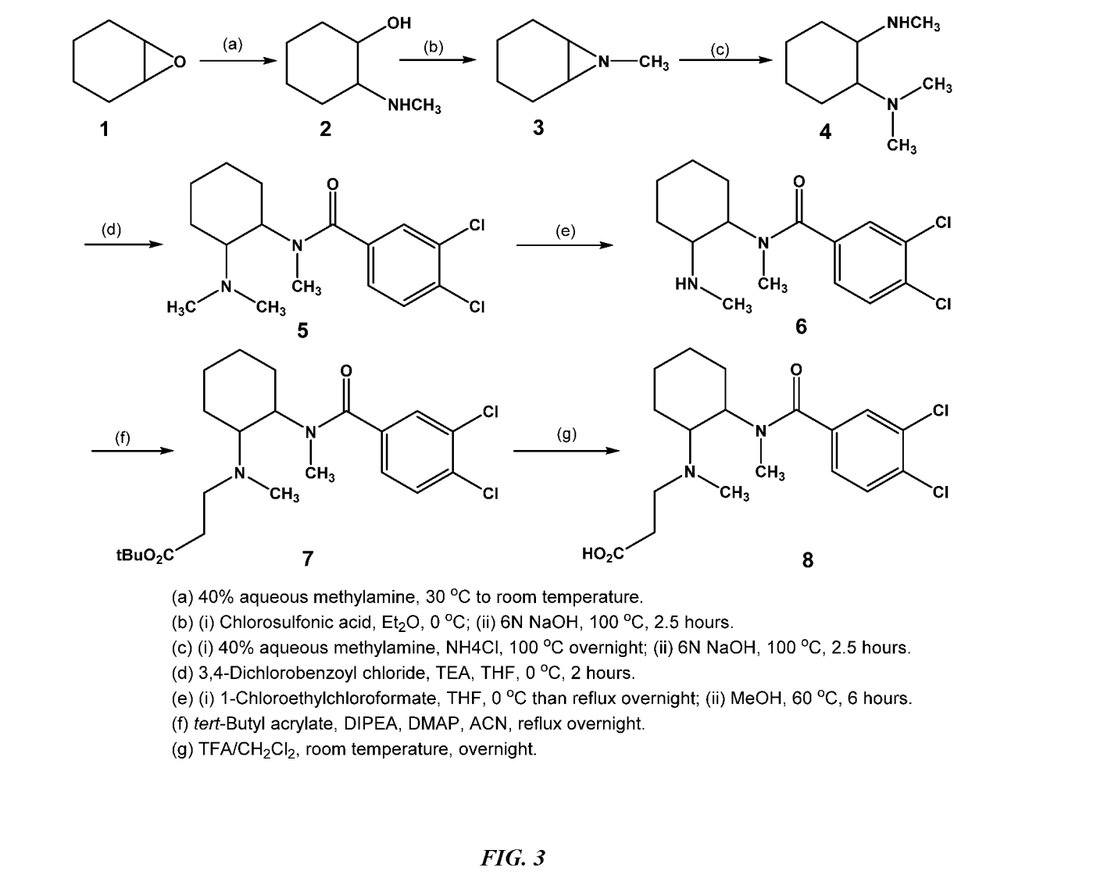
FIG. 3 shows Synthesis of N-desmethyl U-47700 N-propanoic acid (Hapten 1).

Numbers in bold refer to structures in FIG. 3.

Example 1: Synthesis of Trans-2-Methylamino-Cyclohexanol 2

Cyclohexene oxide 1 (20.24 mL, 200.0 mmol) was added dropwise, at RT, over a 1 hour period to 40% aqueous methylamine (51.94 mL, 600.0 mmol). Temperature was maintained for 1 hour below 30° C. with cooling and stirred at RT for 72 h. ON consumption of starting material by TLC, The reaction mixture was heated at 55° C. for 2 hours, to remove the excess of methylamine. The solution was cooled to RT and saturated with solid sodium hydroxide. The mixture was extracted with diethyl ether (2×150 mL). The organic extracts were combined, dried over Na$_2$SO$_4$, filtered and evaporated to dryness, in vacuo, to give trans-2-methylaminocyclohexanol 2 as a crude pale yellow oil (25.8 g, 100%).

Example 2: Synthesis of N-methyl-7-azabicyclo [3.1.0] heptane 3 trans-2-Methylaminocyclohexanol 2 (12.9 g, 99.85 mmol) was dissolved in anhydrous ether (140 mL) under a $N_2$ atmosphere. Chlorosulfonic acid was added dropwise (6.65 mL, 99.85 mmol) at 0° C. Immediate formation of a white solid was observed. Mixture was allowed to stir under $N_2$ at RT for 2.5 hours. Diethyl ether was decanted and the mixture was triturated with additional diethyl ether (140 mL). Residue was cooled to 0° C. and 6N NaOH solution (65 mL, 390.0 mmol) was added dropwise. The mixture was heated at 100° C. for 2.5 hours, cooled to RT and extracted with chloroform (2×100 mL). Organic extracts were combined, dried over $Na_2SO_4$, filtered and evaporated to dryness, in vacuo, to give N-methyl-7-azabicyclo[3.1.0]heptane 3 as a crude colorless oil (10.31 g, 92.7%).

Example 3: Synthesis of trans-N,N-dimethyl-N-methyl-1,2-cyclohexanediamine 4

To a solution of crude N-methyl-7-azabicyclo[3.1.0]heptane 3 (10.31 g, 92.72 mmol) in 40% aqueous methylamine (30.0 mL, 236.44 mmol), was added ammonium chloride (150 mg, 2.78 mmol). The mixture was heated at 100° C. overnight, cooled to rt and 6N NaOH solution (65 mL, 390.0 mmol) was added dropwise. Mixture was heated at 100° C. for 2.5 hours. The mixture was cooled to RT and saturated with solid NaOH. The mixture was then extracted with diethyl ether (2×200 mL). The organic extract was dried over $Na_2SO_4$, filtered and evaporated to dryness, in vacuo, to give trans-N,N-dimethyl-N-methyl-1,2-cyclohexanediamine 4 as a crude yellow oil (9.4 g, 65%).

Example 4: Synthesis of U-47700 5

Crude trans-N,N-dimethyl-N-methyl-1,2-cyclohexanediamine 4 (9.4 g, 60.15 mmol) was dissolved in anhydrous THF (95 mL) under $N_2$, followed by addition of triethylamine (9.21 mL, 66.17 mmol). The solution was cooled to 0° C., and a solution of 3,4-dichlorobenzoyl chloride (12.6 g, 60.15 mmol) in anhydrous THF (95 mL) was added dropwise. During the addition, the solution turned to a slurry and a white precipitate was observed. On completion of addition, the mixture was allowed to stir at RT for 2 hours. EtOAc (100 mL) and water (100 mL) were then added with stirring. The two phases were separated and the aqueous was extracted with EtOAc (100 mL). The organic extracts were combined, dried over $Na_2SO_4$, filtered and evaporated under reduced pressure. Mixture was recrystallized twice using a 1:1 mixture of EtOAc and hexane (2×250 mL) to remove the unwanted by-product a white solid (6.3 g, 20.85 mmol). The filtrate was evaporated to dryness, in vacuo, to give U-47700 5 as a crude white solid (4.3 g, 22%).

Example 5: Synthesis of N-Desmethyl U-47700 6

U-47700 5 (3.3 g, 10.02 mmol) was dissolved in 1,2-dichloroethane (50 mL) under $N_2$, followed by the dropwise addition of 1-chloroethyl chloroformate (1.64 mL, 15.03 mmol) at 0° C. Mixture was heated at reflux overnight. The solvents were removed in vacuo. To the residue was added anhydrous methanol (50 mL) under $N_2$ and heated at 60° C. for 6 hours. The solvents were removed, in vacuo, to give desmethyl U-47700 6 as a crude white solid (4.15 g, 100%).

Example 6: Synthesis of N-Desmethyl U-47700 N-Propanoic Acid t-Butyl Ester 7

N-desmethyl U-47700 6 (1.09 g, 2.54 mmol) was dissolved in acetonitrile (20 mL) under $N_2$, followed by addition of N-ethyldiisopropylamine (3.03 mL, 17.78 mmol) and DMAP (3 mg, 0.03 mmol). To this solution, tert-butyl acrylate was added (5.2 mL, 35.56 mmol) and the mixture was heated at reflux overnight. Further portions of N-diisopropylethylamine (DIPEA) (1.51 mL, 8.89 mmol) and tert-butyl acrylate (2.6 mL, 17.78 mmol) were added at RT and the mixture was heated at reflux overnight. The mixture was evaporated in vacuo and the residue was purified by flash chromatography (Silica gel: 30-40% EtOAc in petroleum ether) to furnish compound N-desmethyl-U-47700 N-propionic acid terbutyl ester 7 as an off yellow oil (0.98 g, 2.01 mmol).

Example 7: Synthesis of N-Desmethyl U-47700 N-Propanoic Acid 8 (Hapten 1)

Compound 7 (0.98 g, 2.01 mmol) was dissolved in dichloromethane (15 mL) and trifluoroacetic acid (7 mL) was added at 0 C. The mixture was stirred at RT overnight. Solvents were revoved in vacuo and the crude residue was azetroped with toluene, twice. The crude residue was purified by flash chromatography (Silica gel: 50% MeOH in EtOAc) to give N-desmethyl U-47700 N-propanoic acid 8 (Hapten 1) as a white solid (333 mg, 43%).

Example 8: Synthesis of N-Desmethyl U-47700 N-Acetic Acid HCTL 9

Figure 4:
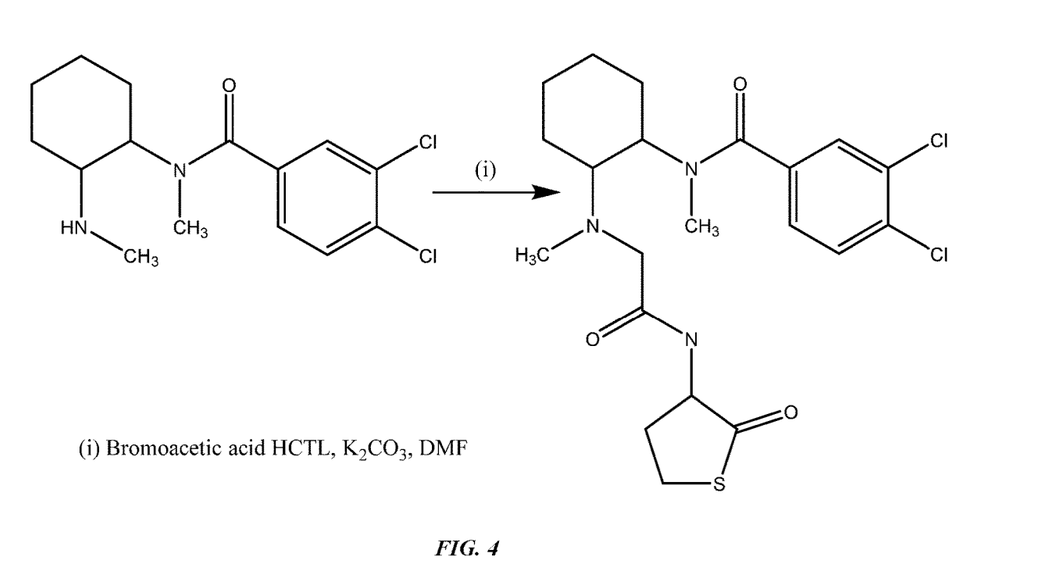
FIG. 4 shows Synthesis of N-desmethyl U-47700 N-acetic acid HCTL (Hapten 2).

To a solution of N-desmethyl U-47700 6 (0.5 g, 1.16 mmol) in anhydrous dimethylformamide (6 mL) under $N_2$, was added potassium carbonate (481 mg, 3.48 mmol) and bromoacetic acid HCTL (homocysteinethiolactone) (333 mg, 1.40 mmol). The mixture was stirred at RT overnight. Additional potassium carbonate (300 mg, 2.17 mmol) and stirred at T for a further night. Solvents were removed in vacuo and the residue was purified by flash give N-desmethyl U-47700 N-acetic acid HCTL 9 (Hapten 2) as a white solid (202.6 mg, 49%).

Example 9: Conjugation of N-Desmethyl U-47700 N-Propionic Acid 8 to BSA (Immunogen 1)

To a solution of N-desmethyl U-47700 N-propionic acid 8 (Hapten 1) (14.8 mg, 0.038 mmol) in DMF (1.0 ml) was added N,N-dicyclohexylcarbodiimide (DCC) (8.53 mg, 0.041 mmol) and N-hydroxysuccinimide (4.76 mg, 0.041 mmol) and the mixture was stirred at room temperature overnight. The dicyclohexylurea formed was removed by filtration and the solution was added dropwise to a solution of BSA (50 mg, 1.5 mmol) in 50 mM sodium bicarbonate solution (pH 8.5) (5 ml). The mixture was then stirred overnight at 4° C. The solution was then dialyzed against 50 mM phosphate buffer pH 7.2 (3 changes) for 24 hours at 4° C., and freeze-dried. MALDI results showed 16.8 molecule of N-desmethyl U-47700 N-propionic acid 8 (Hapten 1) had been conjugated to one molecule of BSA.

Example 10: Conjugation of N-Desmethyl U-47700 N-Propionic Acid 8 to KLH (Immunogen 2)

To a solution of N-desmethyl U-47700 N-propionic acid 8 (Hapten 1) (30.0 mg, 0.077 mmol) in DMF (1.0 ml) was added N,N-dicyclohexylcarbodiimide (DCC) (17.6 mg, 0.082 mmol) and N-hydroxysuccinimide (10.0 mg, 0.085 mmol) and the mixture was stirred at room temperature overnight. The dicyclohexylurea formed was removed by filtration and the solution was added dropwise to a solution of KLH (100.0 mg) in 50 mM sodium bicarbonate solution (pH 8.5) (10 ml). The mixture was then stirred overnight at 4° C. The solution was then dialyzed against 50 mM phosphate buffer pH 7.2 (3 changes) for 24 hours at 4° C., and freeze-dried.

Example 11: Conjugation of N-Desmethyl U-47700 N-Propionic Acid 8 (Hapten 1) to HRP EDC hydrochloride (10 mg) was dissolved in water (0.5 ml) and immediately added to a solution of N-desmethyl U-47700 N-propionic acid 8 (Hapten 1) (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialyzed overnight against 10 L of PBS at pH 7.2 at 4° C.

Example 12: Conjugation of N-Desmethyl U-47700 N-Acetic Acid HCTL 9 (Hapten 2) to HRP 4-N-Maleimidomethylcyclohexyl-1-carboxylic acid NHS ester solution (0.84 mg) in N,N-Dimethylformamide (0.045 mL) was added drop-wise to HRP (20 mg) dissolved in 50 mM HEPES solution, pH8.5 (0.8 mL) while stirring protected from light. And then the resulting solution was stirred at 15-25° C. for 40 minutes. Excess 4-N-Maleimidomethylcyclohexyl-1-carboxylic acid NHS ester was removed by dialysis against Phosphate Buffered Saline, pH 7.2. Keep the solution protected from light during the process. The N-desmethyl U-47700 N-acetic acid HCTL 9 (Hapten 2) (2 mg) was dissolved in N,N-Dimethylformamide (0.2 mL). 0.2 mL of 1M Potassium hydroxide solution was added to the above hapten solution while stirring during 10 minutes period. And then 0.5 mL of 0.2M Phosphate buffer, pH7.0 was added to quench reaction; 0.15 mL of 1M HCl solution was added to bring pH to 7.0. The modified HRP was added to the activated hapten, roll for 2 hours at 15-25° C., and then transfer to 2-8° C. roll for 16-20 hours. Excess hapten was removed with PD-10 column (Pharmacia), pre-equilibrated with Phosphate Buffered Saline, pH 7.2, followed by dialysis at 2-8° C. against Phosphate Buffered Saline, pH 7.2.

Preparation of Antisera

Pre-immunization blood samples are collected from young adult, female, Texel sheep.

In order to generate polyclonal antisera, 2 mgs of the immunogen-2 is prepared in PBS, mixed at a ratio of 50% immunogen in PBS to 50% Freund's Complete adjuvant (Sigma, Product Number F5881) and emulsified by repeatedly passing the mixture through a tip on the end of a 1 ml syringe, until it reaches the required semi-solid consistency. 1 ml of the emulsified mixture is injected intramuscularly into each host animal (sheep) as the primary immunization dose. Further injections (boosts) are prepared (1 mg of immunogen is prepared in PBS and mixed at a ratio of 50% Immunogen in PBS/50% Freunds Incomplete adjuvant, Sigma, Product Number—F5506). Boost injections are delivered intramuscularly at monthly intervals, 1 ml per animal. Serum is sampled monthly by collection of whole blood from the jugular vein for evaluation of the antibody titre. The degree of antibody purification required depends on the intended application. For many purposes, there is no requirement for purification of the serum, however, in other cases, such as where the antibody is to be immobilized on a solid support, purification steps (such as caprylic acid/ammonium sulphate precipitation) can be taken to remove undesired material and eliminate non-specific binding.

Immunoassay

Immunoassay development follows a standard process. A detecting agent (hapten conjugated to HRP) is added to a sample containing the target analyte and the raised antibodies, promoting competition between the detecting agent and analyte for binding to the antibodies. The antibodies are contacted with a solid support; for example, following dilution of the antibodies in coating buffer the antibody-containing buffer is added to the solid support and incubated, typically at approximately 37° C. for about 2 hours, to allow antibody binding to surface. The antibodies can be polyclonal or monoclonal using standard techniques. The signal emitted in the immunoassay is proportionate to the amount of detecting agent bound to the antibodies which in turn is inversely proportional to the analyte concentration. The signal can be detected or quantified by comparison with a calibrator which comprises known levels of target analyte. The cross-reactivity (CR) can be calculated using the equation below in which calculations are based upon binding and displacement at the 50% of maximum OD (optical density) binding point. The maximum OD is the signal generated using tracer alone and 50% displacement (inhibition) corresponds to the $IC_{50}$.

% CR=(OD without cross-reactant−OD with cross-reactant)×100

Using the above immunoassay development method (solid support=polystyrene, polyclonal antibodies from immunogen-2, temp=37° C., incubation 2 hours, using Hapten 2 as tracer) and quantification method the following % CR results were arrived at

TABLE 1

| | 16/T/0999/1927/TM RS3706 | |
| --- | --- | --- |
| | $IC_{50}$ ng/ml | % CR |
| U-47700 | 0.722 | 100.00% |
| AH-7921 | >>20.000 | <<3.610 |
| Desmethyl U-47700 | 3.61 | 20 |
| MT-45 | >>20.000 | <<3.610 |
| Nor AH-7921 | >>20.000 | <<3.610 |
| U-50488 | >>20.000 | <<3.610 |

Figure 5:
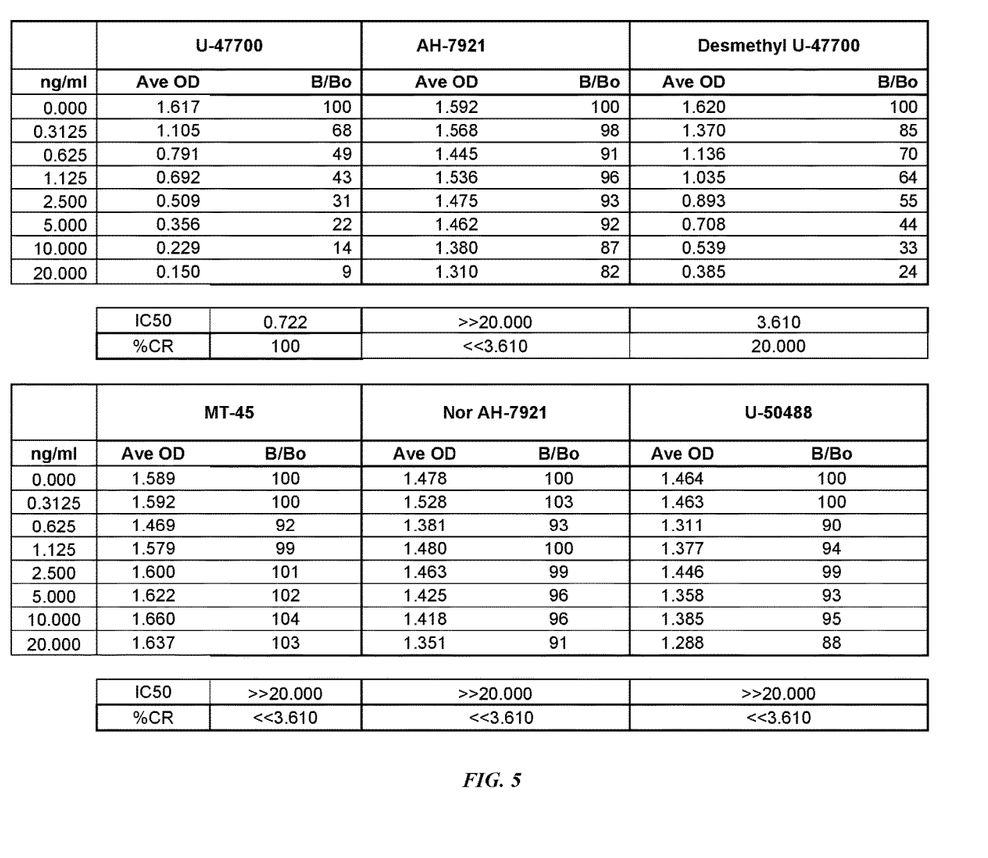
FIG. 5 shows Immunoassay data corresponding to Table 1.

OD = optical density
$IC_{50}$ = standard concentration which produces 50% inhibition of maximal signal
CR = cross-reactivity The data of Table 1 details antibodies which bind to U-47700 and its main metabolite but not to structurally related opiates. Further sheep immunized with immunogens of the invention produced antibodies with similar profiles in the immunoassay method described e.g. Immunogen 2 and Hapten 2 as tracer gave a % CR to U-47700 of 100% compared to 17.30% for desmethyl U-47700 ($IC_{50}$ 2.140 ng/ml to U-47700) and no measurable cross-reactivity to AH-7921, MT-45, nor AH-7921 and U-50488, Immunogen 2 and Hapten 1 as tracer gave a % CR to U-47700 of 100% compared to 23.40% for desmethyl U-47700 (IC$_{50}$ 0.741 ng/ml to U-47700) and no measurable cross-reactivity to AH-7921, MT-45, nor AH-7921 and U-50488.

Similar cross-reactivity results were obtained using an NPS II biochip assay on the Evidence Investigator platform, which is a semi-automated benchtop platform that facilitates simultaneous detection of multiple drug metabolites from a single sample (Randox Laboratories Ltd, Crumlin, Northern Ireland, UK). The results are presented in Table 2.

TABLE 2

| Compound | % CR |
| --- | --- |
| U-47700 | 100.0 |
| AH-7921 | <1.00 |
| Desmethyl U-47700 | 24.3% |
| MT-45 | <1.00 |
| U-50488 | <1.00 |

AH-7921 and nor-AH-7921 are structural isomers of U-47700 and desmethyl U-47700 respectively, and any mass spectrometry-based method of U-47700 and metabolite identification in a sample requires pre-chromatographic separation of AH-7921-based compounds (Jones 2017). The more simplistic method described herein does not require the use of two analytical techniques.

The invention claimed is:

1. A polyclonal antibody having a cross-reactivity to 3,4-dichloro-N-[2-(dimethylamino)cyclohexyl]-N-methyl-benzamide (U-47700) of 100.00%, <<3.610% for AH-7921, 20% for desmethyl U-47700, <<3.610% for MT-45, <<3.610% for nor AH-7921 and <<3.610% for U-50488, wherein the polyclonal antibody is raised to an immunogen comprising a conjugate of N-desmethyl U-47700 N-propionic acid with Keyhole Limpet Hemocyanin (KLH); and wherein said cross-reactivity is measured in the presence of a conjugate of N-desmethyl U-47700 acetic acid homocysteinethiolactone with horseradish peroxidase (HRP) as a tracer.

2. The polyclonal antibody of claim 1, wherein the polyclonal antibody has an IC50 of 0.722 ng/ml for U-47700, >>20.00 ng/ml for AH-7921, 3.61 ng/ml for desmethyl U-47700, >>20.00 ng/ml for MT-45, >>20.00 ng/ml for nor AH-7921 and >>20.00 ng/ml for U-50488.

3. An immunoassay method of detecting or determining 3,4-dichloro-N-[2-(dimethylamino)cyclohexyl]-N-methyl-benzamide and 3,4-dichloro-N-[2-(methylamino) cyclohexyl]-N-methylbenzamide in a solution or an in vitro sample taken from an individual with one or more detecting agents and the polyclonal antibody of claim 1; measuring the signal or signals produced by the one or more detecting agents; and deducing the presence of, or amount of, 3,4-dichloro-N-[2-(dimethylamino)cyclohexyl]-N-methyl benzamide and 3,4-dichloro-N-[2-(methylamino)cyclohexyl]-N-methylbenzamide.

4. A substrate comprising the polyclonal antibody of claim 1.

5. The substrate of claim 4, wherein the substrate is a microtitre plate or a biochip.

6. The substrate of claim 5, wherein the biochip is a ceramic biochip.

7. A kit comprising the polyclonal antibody of claim 1.

8. A method of making an antibody comprising:
administering an immunogen comprising a conjugate of N-desmethyl U-47700 N-propionic acid with Keyhole Limpet Hemocyanin (KLH) to a mammal; and purifying the resultant antibody.

9. The method of claim 8, wherein the antibody is polyclonal.

* * * * *